United States Patent [19]

Markussen et al.

[11] Patent Number: 5,733,763
[45] Date of Patent: Mar. 31, 1998

[54] ENZYME GRANULATE FORMED OF AN ENZYME-CONTAINING CORE AND AN ENZYME-CONTAINING SHELL

[75] Inventors: Erik Kjær Markussen, Værløse; Per Falholt, Gentofte, both of Denmark

[73] Assignee: Novo Nordisk A/S, Bagsvaerd, Denmark

[21] Appl. No.: 432,336

[22] Filed: May 1, 1996

Related U.S. Application Data

[63] Continuation of Ser. No. 973,103, Nov. 6, 1992, abandoned, which is a continuation-in-part of Ser. No. 688,547, Jun. 21, 1991, abandoned, Ser. No. 688,570, Jun. 21, 1991, abandoned, and Ser. No. 843,601, Feb. 28, 1992, abandoned, said Ser. No. 843,601, is a continuation of Ser. No. 234,162, Aug. 19, 1988, abandoned.

[51] Int. Cl.⁶ ............... C12N 11/18; C12N 9/98; C12N 11/14; C11D 7/42
[52] U.S. Cl. ............... 435/175; 435/176; 435/177; 435/182; 510/392; 510/530
[58] Field of Search ............... 435/175, 176, 435/177, 179, 180, 182, 183, 187, 188; 252/DIG. 12; 510/392, 530

[56] References Cited

U.S. PATENT DOCUMENTS

| | | | |
|---|---|---|---|
| 3,723,327 | 3/1973 | van Kampen et al. | 252/110 |
| 4,106,991 | 8/1978 | Markussen et al. | 435/187 |
| 4,661,452 | 4/1987 | Markussen et al. | 435/187 |
| 4,689,297 | 8/1987 | Good et al. | 435/174 |
| 4,707,287 | 11/1987 | Herdeman | 252/91 |
| 4,740,469 | 4/1988 | Nishinaka et al. | 435/187 |
| 4,767,557 | 8/1988 | Herdeman | 252/91 |
| 4,876,198 | 10/1989 | Markussen | 435/183 |
| 4,940,665 | 7/1990 | Iijima et al. | 435/187 |
| 4,965,012 | 10/1990 | Olson | 252/174.12 |
| 4,973,417 | 11/1990 | Falholt | 252/95 |
| 5,093,021 | 3/1992 | Coyne et al. | 252/91 |

FOREIGN PATENT DOCUMENTS

| | | |
|---|---|---|
| 0 271 153 | 6/1988 | European Pat. Off. . |
| 0 286 773 | 10/1988 | European Pat. Off. . |
| 0 304 332 | 2/1989 | European Pat. Off. . |
| 58-179492 | 12/1982 | Japan . |
| 60-37983 | 2/1985 | Japan . |
| 60-37984 | 2/1985 | Japan . |
| WO 89/08694 | 9/1989 | WIPO . |

*Primary Examiner*—David M. Naff
*Attorney, Agent, or Firm*—Steve T. Zelson, Esq.; Valeta Gregg, Esq.

[57] ABSTRACT

An enzyme-containing granulate is prepared containing a core and a shell wherein the core and/or shell contain an enzyme and the shell contains artificial or cellulose fibers in an amount of 1.5–40%. The core may also contain the fibers in an amount of 1.5–40%. In a preferred embodiment, the core contains a primary enzyme, the fibers, a coating of a sustained release agent, and the shell contains a secondary enzyme and the fibers. The sustained release coating causes the primary enzyme to be released more slowly than the secondary enzyme in a washing solution. In another embodiment, the core contains a primary detergent additive, a coating of a protective agent, and the shell contains a secondary detergent additive and the fibers. The protective coating separates the primary and secondary detergent additives so they do not harm each other during storage. Preferably, the core and shell also contain a binder, a filler and a granulating agent. The core preferably is in an amount of 10–50% of the granulate and has an average particle size of between about 100 μm and 1000 μm. The fibers preferably have an average length of 50–2000 μm and an average width of 5–50 μm. The granulates are produced by sequentially introducing the core, the sustained release or protective agent, if present, and the components of the shell into a granulating device such as a drum granulator.

23 Claims, 4 Drawing Sheets

ENZYME GRANULATE FORMED OF AN ENZYME-CONTAINING CORE AND AN ENZYME-CONTAINING SHELL

CROSS REFERENCE TO RELATED APPLICATIONS

This application is a continuation of application Ser. No. 07/973,103, filed Nov. 6, 1992, now abandoned, which is a continuation-in-part of applications Ser. Nos. 07/688,547 and 07/688,570, both filed Jun. 21, 1991, both now abandoned, and of application Ser. No. 07/843,601, filed Feb. 28, 1992, now abandoned, which is a continuation of application Ser. No. 07/234,162, filed Aug. 19, 1988, now abandoned.

TECHNICAL FIELD

This invention relates to enzyme containing granulates and methods for production thereof.

BACKGROUND ART

U.S. Pat. No. 4,106,991 describes a process for drum granulating an enzyme composition including enzyme, finely divided cellulose fibers as 2–40% w/w of the granulate, inorganic salts, and a granulation binder, with a liquid phase granulating agent. Although this known granulate possesses many advantageous characteristics the physical stability of the known granulate is open to improvement.

EP 0 286 773 describes encapsulated enzymes, which in some regards are similar to the detergent additive granulate according to the invention in its broadest aspect. However, the prior art encapsulated enzymes do not contain reinforcing cellulose fibers or artificial fibers in the shell and is not described as being produced by means of the above indicated granulator method, but by means of the fluid bed method, which is not well adapted to production on an industrial scale.

It is an object of this invention to provide a granulate having improved physical stability and other improved properties and a method for producing it.

It is a further object of this invention to provide an improved granulate containing two different detergent additives, in particular a granulate containing two different enzymes, one of which needs to be protected against the other. A "double additive" granulate is advantageous for the soaper, as it reduces the number of additive outlets in the soaper's dosing system.

SUMMARY OF THE INVENTION

In one aspect of the invention it has been found that a granulate built up upon a core, but otherwise substantially as indicated in U.S. Pat. No. 4,106,991, exhibits improved physical stability and other improved characteristics, as will appear from the following. Accordingly, the invention provides an enzyme granulate comprising a core surrounded by a shell comprising cellulose fibers or artificial fibers in an amount of 1.5 to 40% by weight, based on the dry weight of the granulate, except for the core, a binder, a filler, and granulating agents, whereby the core and/or the shell contains an enzyme. The cellulose fibers or the artificial fibers should possess sufficient flexibility to be adaptable to the shape of the cores. The invention also provides a method for production of this granulate.

Due to the introduction of the core, which can be very cheap, the amount of (expensive) cellulose fibers (or artificial fibers) and binder can be reduced below the level indicated in U.S. Pat. No. 4,106,991. Thus, the overall cost of the granulate can be somewhat reduced in comparison to U.S. Pat. No. 4,106,991. Also, it has been found that the physical stability of the granulate is improved over U.S. Pat. No. 4,106,991, due to the reticular structure of the oriented fibers. Also, probably due to the interplay between the core and the fibers circumscribed around the core it has been found that it is possible to produce a granulate with a higher enzymatic activity in comparison to the prior art. Furthermore, as will be explained later in more detail, it is possible in a simple way to obtain the granulate in a very narrow particle size distribution, which can be tailor made to any need.

The introduction of a core and auxiliary agents which are either dissolved or suspended as extremely fine particles, in a particulate material produced with a fluidized bed is known, but the introduction of both a core and fibers in granulate products made by drum granulation is novel. It is believed that the new combination of the core and the cellulose fibers or artificial fibers, which can circumscribe themselves around the core as a coherent reticular structure, is the reason for the extraordinary high physical strength of the granulate according to the invention.

Even when the granulator and the mixtures being granulated according to practice of this invention are exactly according to practice of U.S. Pat. No. 4,106,991, the products are not. The significant differences in the granulate product are alluded to above. It is believed that in the particles produced according to practice of U.S. Pat. No. 4,106,991, the fibers are largely dispersed randomly at all attitudes in three dimensions within the granulate particle. It is believed also that when the particles are granulated around a core according to practice of this invention the fibers largely become layered circumferentially around the core as some sort of non-woven net that contains in the interstices therein the non-fibrous components, i.e. enzyme, filler, binder etc.

A second aspect of the invention provides a granulate with an enzyme in the core (here identified as the primary enzyme) and another enzyme in the shell (here identified as the secondary enzyme). This enzyme containing granulate comprises a core with a primary enzyme and cellulose fibers or artificial fibers in an amount of between 1.5 and 40% by weight, based on the weight of the core, preferably between 5 and 20% by weight, based on the weight of the core, surrounded by a shell comprising a binder, a filler, and granulating agents, and a secondary enzyme, and a sustained release coating between the core and the shell.

Due to the sustained release coating between the core and the shell the secondary enzyme is released quickly in the washing solution and the primary enzyme is released slowly. This represents a broadening of the possibilities for sequential treatment in a washing solution and is particularly advantageous in cases where the secondary enzyme is sensitive to the primary enzyme. The purpose of the invention can be fulfilled also by means of a granulate comprising a mixture of two granulates, i.e. a granulate containing [1] a granulate of the primary enzyme coated with a sustained release coating, and [2] a granulate of the secondary enzyme, which may be coated with a coating which is not a sustained release coating. It is to be understood that such granulate is a technical equivalent to the granulate according to the invention and thus is inside the scope of the invention.

In a third aspect of the invention, the core contains one detergent additive (which may be an enzyme, here identified as the primary detergent additive), and the shell contains another detergent additive (which may be another enzyme, here identified as the secondary detergent additive). The detergent additive granulate according to this aspect of the invention comprises a core with a primary detergent additive surrounded by a shell comprising a secondary detergent additive, a binder, and granulating agents, and optionally a filler, and a protective coating between the core and the shell, whereby the shell comprises cellulose fibers or artificial fibers, preferably in an amount of between 1.5 and 40% by weight of the shell, more preferably between 5 and 20% by weight of the shell, and whereby the core optionally comprises cellulose fibers or artificial fibers, preferably in an amount of between 1.5 and 40% by weight of the core, more preferably between 5 and 20% by weight of the core.

Due to the protective coating between the core and the shell the two detergent additives do not harm each other during storage. This is important in those cases where the primary detergent additive should be protected against the secondary detergent additive and/or environmental factors, e.g. in cases where an enzyme is degraded by a bleaching agent and humidity in the atmosphere, or vice versa. Only during the application during wash the two detergent additives will be brought into contact with each other. Also, due to the content of the cellulose fibers or the artificial fibers in the shell the physical strength of the granulate is high. Furthermore, it surprisingly has been found that a granulator method of production can be easily controlled, also with two non-enzymatic detergent additives, and it can easily be adapted for an industrial scale.

DETAILED DESCRIPTION OF THE INVENTION

Enzyme

Any enzyme can be granulated by means of the process according to the present invention. Preferably, the enzyme is a protease, an amylase, a lipase, an amidase, a cellulase, or an oxidase. These are the most common enzymes in granulate form for industrial purposes. Specific examples are ALCALASE® (a *Bacillus licheniformis* proteinase), ESPERASE® and SAVINASE® (microbial alkaline proteinases produced according to U.S. Pat. No. 3,723,250), CELLUZYME® (a Humicola insolens cellulase according to U.S. Pat. No. 4,435,307), and TERMAMYL® (a *Bacillus licheniformis* amylase). The enzyme can be introduced into the granulator as a pre-dried milled powder or as a solution, for example a concentrated enzyme solution prepared by ultrafiltration, reverse osmosis or evaporation.

In the double-enzyme granulate according to the invention, the core contains one enzyme (the primary enzyme), and the shell contains a different enzyme (the secondary enzyme). Generally the primary enzyme is usually a protease and the secondary enzyme is generally a protease labile enzyme. The secondary enzyme can be a non-proteolytic enzyme, e.g. a lipase, a cellulase, an amylase, a peroxidase, an amidase or an oxidase, or it can be a different protease. As an example, the primary enzyme could be ALCALASE®, SAVINASE® or ESPERASE®, and the secondary enzyme could be a protease which is sensitive to the primary protease, whereby a synergistic effect could be obtained by means of the combination of primary and secondary protease.

In a preferred embodiment of the granulate according to the invention the primary enzyme is ALCALASE®, SAVINASE®, and/or ESPERASE® and the secondary enzyme is a lipase, e.g. LIPOLASE®. A satisfactory sustained release effect during washing will be obtained.

Primary and secondary detergent additive

In a preferred embodiment of the granulate according to the invention the core or the shell contains an enzyme. An enzyme is a typical detergent additive which needs protection from aggressive detergent components.

Examples of pairs of primary and secondary detergent additives are the following: (optical brightener)-(enzyme), (enzyme)-(optical brightener), (enzyme)-(bleach activator), (bleach activator)-(enzyme), (bleach activator)-(optical brightener), (optical brightener)-(bleach activator), (enzyme-chlorine scavenger), (bleach activator-chlorine scavenger), (optical brightener-chlorine scavenger), (bleaching agent)-(enzyme), and (enzyme)-(bleaching agent).

Core material

The core can be made up of any coherent, non crumbling material which will not cause any damage during the end use of the enzyme granulate. Thus, if the enzyme granulate is to be used as a detergent additive, the core could be inorganic or organic salts, which are easily or sparingly soluble in water, e.g. sodium chloride, sodium sulphate, sodium tripolyphosphate or sodium citrate. If the enzyme granulate is to be used as a nutrient additive, the core could be starch, sugar or protein.

Also, the core may be a particle of an already produced enzyme granulate. In this manner granulates with different enzymes in the core and the shell may be produced. Thus, granulate according to the invention may contain enzyme in the core, in the shell or both.

Fibers

The granulate according to the invention contains 1.5–40% of fibers in the core or the shell or both. The preferred fibers used in the granulate are cellulose and artificial (or man-made) fibers.

Preferably, the fibers have an average fiber length of 50–2000 μm, preferably 100–1000 μm, and an average fiber width of 5–50 μm, preferably 10–40 μm. Hereby a satisfactory mechanical strength is obtained.

The cellulose in fibrous form can be sawdust, pure fibrous cellulose, cotton, or other forms of pure or impure fibrous cellulose. Preferably, the cellulose fibers have a maximum fiber length in the range 150–500 μm, average fiber length in the range 30–160 μm, maximum fiber width about 45–50 μm, and average fiber width about 25–30 μm. Several brands of cellulose in fibrous form are on the market, e.g. CEPO S/20, CEPO SS/200 (both products of Sweden) and ARBOCEL. Approximate values for CEPO S/20 are maximum fiber length 500 μm, average fiber length 160 μm, maximum fiber width 50 μm and average fiber width 30 μm. Approximate values for CEPO SS/200 are maximum fiber length 150 μm, average fiber length 50 μm, maximum fiber width 45 μm and average fiber width 25 μm.

Typical artificial fibers are made of polyethylene, polypropylene, polyester, especially Nylon, polyvinylformal, and poly(meth) acrylic compounds.

Preferably, the amount of fibers is between 4 and 20% by weight based on the dry weight of the granulate, except for the core. Below 4% by weight of fibers no satisfactory fiber effect is obtained, and above 20% by weight of fibers the production gets cumbersome and the product expensive.

Sustained-release coating

The sustained release coating can be any sustained release coating used in the art, which does not hurt the primary or secondary enzyme or in other manner disturbs the manufacturing process or the application of the granulate. Examples of usable sustained release coating agents are those described in WO 87/07292, WO 89/08694 (published on Sep. 21, 1989), and in C. A. Finch: Polymers for microcapsule walls, Chemistry and Industry, Nov. 18, 1985 (p. 752).

In a preferred embodiment of the granulate according to the invention the sustained release coating is a material comprising a mono- and/or di- and/or triglyceride of a fatty acid or fatty acids. It has been found that in this embodiment a most satisfactory sustained release action during the washing process can be obtained. Some specific examples are glyceryl palmitate/stearate, hydrogenated tallow and hydrogenated fatty acid ($C_{16}/C_{18}$).

The sustained release coating may contain a powder such as kaolin to control stickiness. Conveniently, sustained release agent and the powder may be introduced alternately into the granulator.

Protective coating

The protective coating can be any protective coating used in the art, which does not harm the primary or secondary detergent additive or in other manner disturb the manufacturing process or the application of the granulate. Examples of usable protective coatings are: fatty acid esters, alkoxylated alcohols, polyvinyl alcohols, ethoxylated alkylphenols, polyethylene glycols (MW 1000 to 8000), linear alcohol alkoxylates (MW 1450 to 2670), polyvinyl pyrrolidone (MW 26000 to 33000), polymeric nonylphenyl ethoxylates (MW 1975 to 4315), and dinonylphenyl ethoxylate (average MW 6900), fatty acids, e.g. palmitic acid, stearic acid, and arachidonic acid, paraffins, bee wax, waxes, mono-, di- or triglycerides of single fatty acids or mixed fatty acids, fatty alcohols, methyl cellulose, ethyl cellulose, hydroxypropylcellulose, and coconut monoethanol amide.

In a preferred embodiment of the granulate according to the invention the protective coating is a mixture of a mono- and diglyceride of a fatty acid. It has been found that in this embodiment a most satisfactory protective action during the storage can be obtained. Advantageous mixtures described in WO 89/08694 can be used.

In a preferred embodiment of the granulate according to the invention the protective coating contains an antioxidant. Suitable examples of antioxidants or reduction agents are thiosulphates, sulfites, bisulfites, ascorbic acid, ascorbates, or butyl hydroxy toluene. In many cases an even better storage stability can be obtained due to the presence of the antioxidant.

Binder

The binder used in the process according to the invention can be a binder conventionally used in the field of granulation with a high melting point or with no melting point at all and of a non waxy nature, e.g. polyvinyl pyrrolidone, dextrin, polyvinyl alcohol, and cellulose derivatives, including for example hydroxypropyl cellulose, methyl cellulose or CMC.

The amount of binder is preferably from 0 to 15% by weight.

Filler

The filler is used for the purpose of adjusting the enzyme activity in the finished granulate. The enzyme introduced into the granulator generally contains diluent impurities which may be considered as fillers, so additional filler may not be needed to standardize the enzymatic activity of the granulate.

Examples of fillers are organic or inorganic salts, which may be soluble or insoluble in water, e.g. $Na_2SO_4$, $NaCl$, $CaCO_3$, minerals, silicates, e.g. kaolin and bentonite, but other inert fillers which do not interfere adversely with the later use of the product can be used. In a preferred embodiment, filler consisting of or comprising inorganic salt is added. Hereby a cheap granulate is obtained.

Particle size and shape

In a preferred embodiment of the granulate according to the invention the core has a mean particle size between 100 and 1000 μm, preferably 200–700 μm. This corresponds to the particle sizes most often required by the users.

In a preferred embodiment of the granulate according to the invention the core is of a shape corresponding to a ratio between the largest and the smallest dimension below 3, preferably below 2, more preferably below 1.5. A satisfactory coating around the core is obtained when the shape of the core is relatively close to spherical.

Preferably, the amount of the core is between 5 and 75% or between 5 and 85% by weight of the granulate, preferably between 10 and 50%, and most preferably between 15 and 40%. If the amount of the core is above 75%, the physical strength tends to be unsatisfactory, and in the case of a double-enzyme granulate the loading of a sufficient amount of a secondary enzyme will be difficult. If the amount of the core is less than 5%, the advantages associated with the core are not obtained, and in the case of a double-enzyme granulate the loading of a sufficient amount of a primary enzyme will be difficult.

Coating

In a preferred embodiment of the granulate according to the invention the shell is surrounded by a final dust suppressing coating. This is advantageous in those cases where the shell tends to produce an unacceptable amount of dust. The dust suppression coating can be applied to the same granulating device used for producing the granulate or on a separate granulating device. This final dust suppressing coating can also in certain cases serve as a further protective coating.

Granulation process

An enzyme containing granulate according to the invention can be produced by the introduction into a granulator of a core, 1.5 to 40% by weight of fibers, optionally a binder, enzyme and filler in an amount which generates the intended enzyme activity in the finished granulate, a liquid granulating agent. Hereinafter, all percentages are relative to the total amount of dry substances, except for the core. The sequence of the introduction of the different materials is arbitrary, but preferably at least the major part of the granulating agent is introduced after at least a substantial part of the dry substances is introduced into the granulator. The granulation is preferably performed at a temperature between 20° and 70° C. After the granulation, the granulate may be dried if necessary.

The method according to the invention can be performed both batchwise and continuously.

A double-enzyme granulate according to the invention may be produced by a method comprising the introduction of a core into a granulating device, and thereafter sequentially introducing a sustained release coating agent, shell material and optionally a final dust suppressing coating agent into the granulating device.

The method for the production of the "double detergent additive" granulate according to the invention comprises the introduction of the core into a granulating drum, whereafter sequentially the protective coating agent, the shell material and optionally a final dust suppressing coating agent, and furthermore cellulose fibers or artificial fibers in the appropriate amounts and at the appropriate stages, are introduced into the granulating drum.

Furthermore, optional additives such as coloring agents, pigments, disintegrants, or enzyme stabilizers, e.g. antioxidants, may be added.

Granulator

The granulator can be any of the known types of mixing granulators, drum granulators, pan granulators or modifications of these. If a mixing granulator is used, for example a mixing drum from the company Gebr. Lödige Maschinen G.m.b.H, 479 Paderborn, Elsenerstrasse 7–9, Germany, it is preferred that small rotating knives are mounted in the granulator in order to compact the granules. It is to be understood that the term drum granulator represents a broad category of granulator devices, comprising for instance pan granulators and granulation mixers.

Any granulating device can be used in relation to the method according to the invention, e.g. a granulating drum, a fluid bed coater or the granulating device described in WO 85/05288. The entire process can be carried out in one of these granulating devices, or the core can be coated with a sustained-release or protective coating in one granulating device, whereafter the coated core can be isolated and transferred to another granulating device for application of the shell, whereafter if wanted application of a dust suppression coating can be performed on the same granulating drum or another granulating drum.

Granulating agent

The granulating agent is preferably water and/or a waxy substance. Preferably, the amount of granulating agent is in the range of from 5 to 70% by weight, whereby the maximum amount of waxy substance is 70% by weight and the maximum amount of water is 70% by weight.

The granulating agent is used as a liquid phase in the granulation process; the waxy substance if present therefore is either dissolved or dispersed in the water or melted. A waxy substance is a substance which possesses all of the following characteristics: (1) the melting point is between 30° and 100° C., preferably between 40° and 60° C., (2) the substance is of a tough and not brittle nature, and (3) the substance possesses substantial plasticity at room temperature.

Both water and the waxy substance can act as granulating agents, i.e. they are both active during the formation of the granules, the waxy substance stays as a constituent in the finished granules, whereas the majority of the water is removed during subsequent drying. Thus in order to refer all amounts to the finished, dry granules all percentages are calculated on the basis of total dry substances, which means that water, one of the granulating agents, is not added to the other constituents when calculating the percentage of water, whereas the waxy substance, the other granulating agent, has to be added to the other dry constituents when calculating the percentage of waxy substance. Examples of waxy substances are polyglycols, fatty alcohols, ethoxylated fatty alcohols, higher fatty acids, mono-, di- and triglycerolesters of higher fatty acids, e.g. glycerol monostearate, alkylaryethoxylates and coconut monoethanolamide.

If a high amount of waxy substance is used, relatively little water should be added, and vice versa. Thus the granulating agent can be either water alone, waxy substance alone or a mixture of water and waxy substance. In case a mixture of water and waxy substance is used, the water and the waxy substance can be added in any sequence, e.g. first the water and then the waxy substance, or first the waxy substance and then the water or a solution or suspension of the waxy substance in the water. Also, in case a mixture of water and waxy substance is used, the waxy substance can be soluble or insoluble (but dispersible) in water.

Drying

If no water is used in the granulating agent, usually no drying is needed. In this case the granulating agent is a melted waxy material, and only cooling is needed to solidify the particles. In most cases, however, some drying is performed, and the drying is usually carried out as a fluid bed drying whereby small amounts of dust and small granules are blown away from the surface of the granules. However, any kind of drying can be used. In the instance where no water is used as a granulating agent, a flow conditioner or anticaking agent may be added to the granulate either before or after the cooling step, e.g. fumed silica, for instance the commercial products AEROSIL or CAB-O-SIL.

EXAMPLES

The invention will be illustrated by the following examples. The activity units used in the examples are defined as follows.

| enzyme | activity unit | definition indicated in |
|---|---|---|
| proteolytic | Anson | AF 4.3/5-GB |
|  | KNPU | AF 220/1-GB |
| amylolytic | KNU | AF 215/1-GB |
| lipolytic | LU | AF 95/4-GB |
| cellulolytic | CSU | AF 253/2-GB |

On request these AF publications can be obtained from NOVO NORDISK A/S (previously Novo Industri A/S), Novo Allé, 2880 Bagsvaerd, Denmark.

In the examples the core material exhibited a cubical shape in case the core was NaCl, and a rounded, irregular shape in case the core was $Na_2SO_4$.

Example 1

9.0 kg of NaCl core material with a particle size between 250 and 300 µm was introduced into a Lödige mixer FM 130 D/1 MZ and was mixed with 5.2 kg of SAVINASE concentrate (34 KNPU/g)

3.0 kg of fibrous cellulose, Arbocel BC 200

1.2 kg of $TiO_2$ 1.5 kg of adhesive carbohydrate 10.1 kg of finely ground Na2SO4

The total charge of 30 kg of dry matter was sprayed with 4.0 kg of water as described in Example 1 in U.S. Pat. No. 4,106,991, and a post granulation for 5 minutes was performed with the rapidly rotating set of knives (vide FIG. 3 in Danish Patent No. 146857, corresponding to U.S. Pat. No. 4,106,991), whereby the powder components distributed themselves evenly and in a compact manner around the core surfaces. The moist granulate was dried in a fluid bed, whereby a product was obtained with the following properties.

Core: 30%, Shell: 70%

Enzyme activity: 5.3 KNPU/g

Particle size distribution:

3.5 %>1000 µm 5.0%>850

6.8%>710
11.0%>600
17.0%>500
42.0%>420
65.0%>355
77.0%>300
90.0%>250
3.5%<210
1.9%<180
0.1%<150

Mean diameter: 390 μm

The amount of dust and the physical strength were measured according to two different methods:

A. Elutriation dust method, as described in NOVO publication AF 129/3-GB, available on request from NOVO NORDISK A/S B. Novo attrition dust method, as described in NOVO publication AF 225/1-GB, available on request from NOVO NORDISK A/S It appears from the following table that the values in regard to dust and physical strength of the granulate according to this example were superior to the corresponding prior art values.

| Method | Invention, this example | | Prior art (U.S. Pat. No. 4,106,991) | |
|---|---|---|---|---|
| | total, mg | active, μg (4 KNPU/g) | total, mg | active, μg (4 KNPU/g) |
| A | 15.4 | 8800 | 10–30 | 10,000–20,000 |
| B | 11.9 | 4100 | 10–20 | 10,000–20,000 |

Example 2

7.5 kg of $Na_2SO_4$ core material with a particle size between 300 and 500 μm was introduced into a Lödige mixer FM 130 D/IMZ and mixed with 9.0 kg of SAVINASE concentrate (28 KNPU/g)

3.38 kg of fibrous cellulose Arbocel BC 200

0.9 kg of $TiO_2$ 7.5 kg of finely ground $Na_2SO_4$

The total charge was sprayed with 6.4 kg of binder solution (a 27% aqueous solution of adhesive carbohydrates). The granulate was processed and dried as described in Example 1, whereby a product was obtained with the following properties:

Core: 25%, shell 75%

Enzyme activity: 8.0 KNPU/g

Particle size distribution:

6.7 %>1000 μm
7.5%>850
11.0%>710
16.0%>600
34.0%>500
62.0%>425
78.0%>355
90.0%>300
4.0%<250
1.9%<210
0.9%<180

Mean diameter: 450 μm

The amount of dust and the physical strength appears from the following table.

| Method | total, mg | active, μg (4 KNPU/g) |
|---|---|---|
| A | 3.8 | 1390 |
| B | 9.4 | 3900 |

Example 3

6.0 kg of trisodium citrate.$2H_2O$ core material with particles of rounded, irregular shape and a particle size distribution as indicated below was introduced into a Lödige mixer FM 50 and was mixed with 2.2 kg of SAVINASE concentrate (38 KNPU/g)

0.6 kg of $TiO_2$ 0.7 kg of adhesive carbohydrate 1.5 kg of fibrous cellulose Arbocel BC 200

5.0 kg of finely ground $Na2SO_4$

The total charge was sprayed with 2.0 kg of water, and processing and drying was carried out as indicated in Example 1, whereby a product was obtained with the following properties:

Particle size distribution:

| | Sodium citrate core | Product |
|---|---|---|
| >1000 μm | | 15 |
| >850 μm | | 19 |
| >707 μm | | 26 |
| >600 μm | 1.2 | 42 |
| >500 μm | 20 | 64 |
| >420 μm | 50 | 83 |
| >755 μm | 70 | 92 |
| <300 μm | 20 | 1.7 |
| <250 μm | 10 | 0.5 |

Mean diameter: 565 μm

The amount of dust and the physical strength appears from the following table.

| Method | total, mg | active, μg (4 KNPU/g) |
|---|---|---|
| A | 4.8 | 4800 |

Example 4

In this example the shell was placed onto the core in two steps, as indicated in the following.

Step 1

7.5 kg of sodium sulphate core material with particle sizes between 300 and 500 μm was introduced into a Lödige mixer FM 50 and was mixed with 4.5 kg of SAVINASE concentrate (28 KNPU/g)

1.7 kg of fibrous cellulose, Arbocel BC 200

0.45 kg of $TiO_2$ 3.75 kg of finely ground $Na_2SO_4$

The mixed dry components were sprayed with 3.0 kg of a binder solution (a 27% aqueous solution of adhesive carbohydrates), and the granulate was otherwise treated as in Example 1, but without the drying step.

Step 2

Without removing the moist granulate from step 1 from the mixer it was mixed with 4.5 kg of SAVINASE concentrate (28 KNPU/g)

1.7 kg of fibrous cellulose, Arbocel BC 200

0.45 kg of TiO$_2$ 3.75 kg of finely ground Na$_2$SO$_4$ whereafter 3.0 kg of the same binder solution as the one used in step 1 was sprayed onto the contents of the mixer. The granulate was processed and dried as in Example 1, whereby a product was obtained with the following properties:

Core: 25%, shell 75%

Enzyme activity: 8.7 KNPU/g

Particle size distribution:

| | |
|---|---|
| 4.8% | >1000 μm |
| 6.3% | >850 μm |
| 9.5% | >707 μm |
| 20.0% | >600 μm |
| 47.0% | >500 μm |
| 71.0% | >425 μm |
| 82.0% | >355 μm |
| 89.0% | <300 μm |
| 5.5% | <250 μm |
| 3.0% | <210 μm |
| 1.4% | <180 μm |
| 0.6% | <150 μm |

Mean diameter: 490 μm

The amount of dust and the physical strength appears from the following table.

| Method | total, mg | active, μg (4 KNPU/g) |
|---|---|---|
| A | 2.0 | 1300 |
| B | 8.4 | 7100 |

Example 5

15 kg of a protease core (produced according to U.S. Pat. No. 4,106,991, Example 1, except that Na$_2$SO$_4$ was used as a dilution agent rather than NaCl, and that SAVINASE was used as the proteolytic enzyme rather than ALCALASE) with a particle core of 300–900 μm and with a nearly spherical shape was introduced into a Lödige mixer of type FM 50. At this stage the proteolytic core was provided with a shell containing an amylolytic enzyme (BAN) produced by means of *B. amyloliquefaciens* by mixing the core with a powder.

The composition of the powder was:

0.90 kg of BAN concentrate (925 KNU/g)

0.50 kg of fibrous cellulose, DIACEL 200

0.25 kg of TiO$_2$ 2.90 kg of Na$_2$SO$_4$

The charge consisting of cores and powder was mixed, and 2.05 kg of a 27.3% of an aqueous solution of adhesive carbohydrate was sprayed thereon.

The granulate was treated and dried as described in Example 1, whereby a granulate with the following characteristics was obtained:

Enzyme activity: 4.7 KNPU/g (proteolytic)

36.0 KNU/g (amylolytic)

Particle distribution:

| | |
|---|---|
| 0.8% | >1000 μm |
| 13.5% | >850 μm |
| 41.1% | >707 μm |
| 66.4% | >600 μm |
| 86.7% | >500 μm |
| 95.7% | >425 μm |
| 98.7% | >355 μm |
| 0.06% | <300 μm |

Mean diameter: 660

Dust content: (in 300–900 μm fraction)

| Method | Granulate according to example | | | core | | |
|---|---|---|---|---|---|---|
| A: | 13.0 mg | 1320 μg | 4.0 KNPU/g | 25.1 mg | 8040 μg | 4.0 KNPU/g |
| | 13.5 mg | 452 μg | 240 KNU/g | | | |
| B: | 1.6 mg | 361 μg | 4.0 KNPU/g | 14.0 mg | 5500 μg | 4.0 KNPU/g |
| | 1.7 mg | 327 μg | 240 KNU/g | | | |

Example 6

10 kg of SAVINASE cores of the same kind as the SAVINASE cores described in Example 5 was coated with a powder containing an amylolytic enzyme, whereby the powder forms a shell around the cores. The composition of the powder was as follows:

1.2 kg of BAN (925 KNU/g)

0.5 kg of fibrous cellulose, DIACEL 200

0.2 kg of titanium dioxide 2.3 kg of Na$_2$SO$_4$

The charge consisting of cores and powder was mixed and heated to 40° C., whereafter a solution of 1.2 kg of PEG in 0.6 kg of water was sprayed onto the charge. The granulate was treated and dried as described in Example 1. After drying the granulate was cooled to room temperature, whereby the wax solidifies. Hereby a granulate was obtained with the following characteristics:

Activity: 5.4 KNPU/g 72.0 Knu/g

Particle distribution:

| | |
|---|---|
| 3.3% | >1000 μm |
| 17.3% | >850 μm |
| 40.1% | >707 μm |
| 58.9% | >600 μm |
| 78.2% | >500 μm |
| 91.7% | >425 μm |
| 97.7% | >355 μm |
| 0.9% | <300 μm |

Mean diameter: 630
Dust content: (in 300–900 μm fraction)

| Method | Granulate according to example | | | core | | |
|---|---|---|---|---|---|---|
| A: | 24.8 mg | 217 μg | 4.0 KNPU/g | 21.3 mg | 10800 μ | 4.0 KNPU/g |
|    | 1.1 mg | 4600 μg | 240 KNPU/g | | | |
| B: | 29.5 mg | 1160 μg | 4.0 KNPU/g | 618 mg | 770000 μg | 4.0 KNPU/g |
|    | 30.3 mg | 12800 μg | 240 KNU/g | | | |

Example 7

10 kg of a $Na_2SO_4$ core with particle size 300–500 μm was introduced into a Lödige mixer, type FM 50, in which the core was provided with a shell containing an amylolytic enzyme by means of a three step process, in the following manner.

Initially 10 kg of cores were mixed with a powder consisting of 0.6 kg of BAN (750 KNU/g)
0.3 kg of fibrous cellulose, DIACEL 200
0.2 kg of titanium dioxide
1.3 kg of $Na_2SO_4$ For the sake of brevity this powder is referred to in the following as 2.4 kg of powder $P_1$.

The mixture of cores and powder was heated to 65° C., and this temperature was maintained throughout the entire process. Subsequently 0.7 kg of pure melted PEG 4000 with a temperature of 70° C. was sprayed onto the heated mixture of cores and powder. A granulating treatment was carried out as indicated in Example 1, but just for 1 minutes.

Now another 2.4 kg of powder $P_1$ was introduced into the mixer, followed by 0.5 kg of PEG 4000, and a 1 minute granulating treatment as indicated above.

Then another 2.4 kg of powder $P_1$ was introduced into the mixer, followed by 1.2 kg of PEG 4000, and a 1 minute granulating treatment as indicated above.

Activity: 63 KNU/g
Particle size distribution:

| 0.3% | >1000 μm |
| 0.5% | >850 μm |
| 4.3% | >707 μm |
| 24.4% | >600 μm |
| 54.5% | >500 μm |
| 73.2% | >425 μm |
| 87.1% | >355 μm |
| 97.4 | <300 μm |
| 0.9% | <250 μm |

Mean diameter: 550 μm
Dust content: (in 300–900 μm fraction)
Method:
A: 2.0 mg 327 μg (240 KNU/g)
B: 4.6-717-240

Example 8

13 kg of a $Na_2SO_4$ based core of lipase produced according to EP 258,068 (equivalent to U.S. Pat. No. 4,810,414) with an activity of 26000 LU/g was introduced into a Lödige mixer type FM 50, in which the core was provided with a shell containing SAVINASE protease in a three step process, as follows:

The 13 kg of lipase cores were mixed with a powder consisting of 1.00 kg of ground SAVINASE concentrate of 39.5 KNPU/g
0.12 kg of fibrous cellulose, DIACEL 200
0.09 kg of titanium dioxide
0.91 kg of $Na_2SO_4$ For the sake of brevity this powder is referred to in the following as 2.12 kg of powder $P_2$.

The processing temperature was 20°–30° C.

Then 0.9 kg of a binder solution which was a 25% aqueous solution of an adhesive carbohydrate was sprayed onto the mixture in the Lödige mixer.

Subsequently another 2.12 kg of powder $P_2$ was introduced into the mixer, followed by 0.7 kg of the above indicated binder solution, which was introduced by spraying.

Then another 2.12 kg of powder $P_2$ was introduced into the mixer, followed by 1.15 kg of binder solution, which was introduced by spraying. Finally granulation, compaction and drying was carried out as indicated in Example 1.

A granulate with the following properties was obtained:
Core: 67% by weight, shell 33% by weight
Activity: 17.900 LU/g (lipolytic)
6.0 KNPU/g (proteolytic)
Particle size distribution:

| 2.3% | >1000 μm |
| 12.0% | >850 μm |
| 29.1% | >707 μm |
| 48.7% | >600 μm |
| 71.5% | >500 μm |
| 86.5% | >425 μm |
| 95.1% | >355 μm |
| 3.0% | <300 μm |

Mean diameter: 590 μm
Dust content: (in 300–900 μm fraction)

| Method | Granulate according to example | | | core | |
|---|---|---|---|---|---|
| A: | 3.9 mg | 3360 μg | 4.0 KNPU/g | 32.4 mg | 200 LU/filter |
|    | 6.0 mg | 0 μg LU/filter | | | |
| B: | 1.0 mg | 1340 μg | 4.0 KNPU/g | | |
|    | 1.7 mg | 0 μg LU/filter | | | |

Example 9

Step 1
Core

A granulate with proteolytic activity and with the composition

25% ALCALASE® concentrate (15.1 AU/g)
15% fibrous cellulose, ARBOCEL BC200
4% kaolin, type ECC Speswhite
10% carbohydrate binder
46% finely ground sodium sulphate was produced and dried as described in U.S. Pat. No. 4,106,991, Example 1. The dried granulate with an activity of 3.6 AU/g was sifted and the fraction between 300 μm and 710 μm was further treated as described below in step 2.

Step 2
Sustained release layer

Coating with a sustained release layer of glyceryl stearate/palmitate Grindtek MSP 90 (melting point 68° C.) and kaolin (Speswhite, ECC).

7 kg of sifted granulate according to step 1 was heated in a 20 l Lödige mixer to 75°–80° C. which temperature was kept during the coating process. The coating was applied with continuous mixing and alternately applying melted MSP90 and kaolin in such balanced way that the charge was neither too sticky neither contains a substantial amount of free kaolin powder. In the example the actual sequences and amounts of materials were:

1. 500 g MSP90
2. 1000 g kaolin
3. 300 g MSP90
4. 1000 g kaolin
5. 200 g MSP90
6. 1000 g kaolin
7. 200 g MSP90
8. 1000 g kaolin
9. 200 g MSP90
10. 1000 g kaolin Total: 1.4 kg MSP90 and 5.0 kg kaolin.

Step 2 was completed by cooling the coated granulate on a fluid bed to room temperature and a minor amount (<1%) of non product material was sifted away on a 1.2 mm screen.

The coated granulate had a proteolytic activity of 1.85 AU/g.

Step 3
Shell 10 kg of the granulate with a sustained release coating from step 2 was coated with a shell containing the lipolytic enzyme SP 341, which is the *Pseudomonas cepacia* lipase described in European patent application with publication No. 0214761 (equivalent to U.S. Pat. No. 4876024):

20 kg of shell material with the composition:

30% SP341 concentrate (lipolytic activity 195,000 LU/g)

15% fibrous cellulose ARBOCEL BC200

4% kaolin, ECC Speswhite

51% finely ground sodium sulphate was mixed with and layered on the surface of the 10 kg of granulate from step 2 as described above in Example 1 except that in the present example the core had a proteolytic activity and the shell had a lipolytic activity.

Step 3 was concluded with a fluid bed drying of the granulate to a water content below 1% and sifting between 300 μm and 1200 μm.

Step 4

Coating with 4% PEG 4000 and 10% of a mixture of titanium dioxide:kaolin 1:1 as described in U.S. Pat. No. 4,106,991, Example 22. The product after step 4 had a proteolytic activity of 0.53 AU/g and a lipolytic activity of 31,000 LU/g.

Example 10

Step 1

A granulate with proteolytic activity and with the composition:

22% SAVINASE® concentrate (51 KNPU/g)

15% fibrous cellulose, ARBOCEL BC200

4% kaolin, type ECC Speswhite

10% carbohydrate binder

49% finely ground sodium sulphate was produced as described in Example 9, step 1.

The proteolytic activity of the dried granulate was 10.8 KNPU/g.

Step 2

A sustained release coating was applied as described in Example 9, step 2. The coated granulate had a proteolytic activity of 5.4 KNPU/g.

Step 3

A lipolytic shell with enzyme SP 341 was applied as described in Example 9, step 3.

Step 4

A coating was applied as described in Example 9, step 4. The product after step 4 had a proteolytic activity of 1.54 KNPU/g and a lipolytic activity of 31,300 LU/g.

Example 11

Step 1

A granulate with proteolytic activity and with the composition:

34% ALCALASE® concentrate (15.1 AU/g)

15% fibrous cellulose, ARBOCEL BC200

4% kaolin, type ECC Speswhite

8% carbohydrate binder

39% finely ground sodium sulphate was produced as described in Example 9, step 1. The proteolytic activity of the dried granulate was 4.9 AU/g.

Step 2

A sustained release coating was applied as described in Example 9, step 2. The coated granulate had a proteolytic activity of 2.5 AU/g.

Step 3

10 kg of granulate with sustained release coating from step 2 was coated with a shell containing the lipolytic enzyme LIPOLASE, which is the recombinant Humicola lipase described in European patent application with publication No. 0305216.

10 kg of shell material with the composition:

23% LIPOLASE® concentrate (lipolytic activity 680,000 LU/g)

15% fibrous cellulose ARBOCEL BC200

4% kaolin, ECC Speswhite

10% carbohydrate binder

48% finely ground sodium sulphate was mixed with and layered on the surface of the 10 kg of granulate from step 2 as described in Example 1, except that in the present example the core had a proteolytic activity and the shell had a lipolytic activity, and that a 50 l Lödige mixer FM 50 was used.

Step 3 was concluded with a fluid bed drying of the granulate to a water content below 1% and sifting between 300 μm and 1200 μm.

Step 4

A coating was applied as described in Example 9, step 1. The product after step 4 had a proteolytic activity of 1.08 AU/g and a lipolytic activity of 63,000 LU/g.

Example 12

Step 1

A Savinase® granulate was produced as described in Example 10, step 1, except that the amount of fibrous cellulose in the core was 10% and the amount of carbohydrate binder 8%. The proteolytic activity of the dried granulate was 7.8 KNPU/g.

Step 2

10 kg of core material from step 1, sifted to obtain particle sizes between 400 and 700 µm, was transferred to a 20 liter Lödige mixer and provided with a sustained release coating of MSP 90 and kaolin as described in Example 9, step 2.

Total: 1.0 kg MSP90 and 3.2 kg kaolin.

Step 3

10 kg of the granulate with the sustained release coating from step 2 was coated with a shell containing the cellulolytic enzyme Celluzyme®, which is a commercial cellulase preparation from Novo Nordisk A/S.

10 kg of shell material with the composition:

50% Celluzyme® concentrate

10% fibrous cellulose, ARBOCEL BC200

4% kaolin, type ECC Speswhite

8% carbohydrate binder

28% finely ground sodium sulphate was mixed with and layered on the surface of the 10 kg of granulate from step 2 in the manner described in Example 9, step 3, except that the core had a proteolytic activity and the shell a cellulolytic activity.

The product after step 3 had a proteolytic activity of 3.5 KNPU/g and a cellulolytic activity of 750 CSU/g.

A washing experiment with this granulate was carried out in comparison to a control comprising a mixture of a Savinase® granulate and a Celluzyme® granulate, with comparable activities. It turned out that the cellulase activity/performance in relation to the washing experiment with the granulate according to the invention was higher/better than the cellulase activity/performance in relation to the control.

Example 13

Step 1

A Savinase® granulate was produced as described in Example 12, step 1. The proteolytic activity of the dried granulate was 7.8 KNPU/g.

Step 2

10 kg of core material from step 1, sifted to obtain particle sizes between 400 and 700 µm, was transferred to a 20 liter Lödige mixer and provided with a sustained release coating of hydrogenated tallow with melting point 59° C. and kaolin as described in Example 9, step 2.

Total: 0.3 kg of hydrogenated tallow and 1.0 kg of kaolin.

A further top coating of a hydrophilic nature consisting of 0.5 kg PEG 4000 and 1.7 kg kaolin was applied in the manner described in Example 9, step 2.

Step 3

A cellulolytic shell with the enzyme Celluzyme® was applied as described in Example 12, step 3. The product after step 3 had a proteolytic activity of 3.8 KNPU/g and a cellulolytic activity of 530 CSU/g.

Example 14

Step 1

A Savinase® granulate was produced as described in Example 12, step 1. The proteolytic activity of the dried granulate was 7.8 KNPU/g.

Step 2

10 kg of core material from step 1, sifted to obtain particle sizes between 300 and 1200 µm, was transferred to a 20 liter Lödige mixer and provided with a sustained release coating of hydrogenated tallow and kaolin as described in Example 9, step 2.

Total: 1.0 kg of hydrogenated tallow and 3.7 kg kaolin.

Step 3

10 kg of the granulate with the sustained release coating from step 2 was coated with a shell containing the lipolytic enzyme Lipolase®, which is the recombinant Humicola lipase described in European patent application with publication No. 0 305 216.

10 kg of shell material with the composition:

1.5 kg fibrous cellulose, ARBOCEL BC200

1.0 kg bentonite, Type ASB 350, ECC 1.0 kg carbohydrate binder 6.0 kg finely ground sodium sulphate was mixed with and layered on the surface of granulate from step 2 by spraying with 0.9 kg of a liquid Lipolase® concentrate, produced by ultrafiltration and evaporation, in the manner described in Example 1, except that in the present example the core had a proteolytic activity and the shell a lipolytic activity.

The product after step 3 had a proteolytic activity of 2.7 KNPU/g and a lipolytic activity of 7100 LU/g.

Example 15

Step 1

A granulate with proteolytic activity was produced as described in Example 9, step 1, except that the enzyme was ESPERASE® and except that the amount of fibrous cellulose in the core was 10% and the amount of carbohydrate binder was 8%. The proteolytic activity of the dried granulate was 8.5 KNPU/g.

Step 2

10 kg of core material from step 1, sifted to obtain particle sizes between 300 and 1200 µm, was transferred to a 20 liter Lödige mixer and provided with a sustained release coating of hydrogenated fatty acid ($C_{16}/C_{18}$) with melting point 58° C. and kaolin as described in Example 9, step 2.

Total: 0.8 kg of hydrogenated fatty acid and 2.4 kg kaolin.

Step 3

10 kg of the granulate with the sustained release coating from step 2 was coated with a shell containing an amylolytic enzyme BAN, which is a commercial bacterial amylase preparation from Novo Nordisk A/S.

10 kg of shell material with the composition:

0.2 kg BAN concentrate 1.0 kg fibrous cellulose, ARBOCEL BC200

0.4 kg kaolin, type ECC Speswhite 6.4 kg sodium sulphate was mixed with and layered on the surface of the 10 kg of granulate from step 2 by spraying with 1.4 kg of a carbohydrate binder solution (40% in water). Otherwise the layering was performed as described in Example 9, step 3.

The product after step 3 had a proteolytic activity of 4.3 KNPU/g and an amylolytic activity of 37 KNU/g.

Example 16

Step 1

An Alcalase® granulate was produced as described in Example 9, step 1, except that the amount of fibrous cellulose in the core was 10% and the amount of carbohydrate binder was 8%. The proteolytic activity of the dried granulate was 2.6 AU/g.

Step 2

10 kg of core material from step 1, sifted to obtain particle sizes between 300 and 1200 µm, was transferred to a 20 liter Lödige mixer and provided with a sustained release coating of hydrogenated tallow with melting point 59° C. and kaolin in the manner described in Example 9, step 2.

Total: 0.8 kg of hydrogenated tallow and 2.2 kg kaolin.

19

Step 3

A cellulolytic shell with the enzyme Celluzyme® was applied as described in Example 12, step 3. The product after step 3 had a proteolytic activity of 1.0 AU/g and a cellulolytic activity of 760 CSU/g.

A washing experiment with this granulate was carried out in comparison to a control comprising a mixture of an Alcalase® granulate and a Celluzyme® granulate, with comparable activities. It turned out that the cellulase activity/performance in relation to the invention was higher/ better than the cellulase activity/performance in relation to the control.

Example 17

Washing performance examples were made with a detergent of a composition as listed below:

LAS (Nansa S80/S) 6.5%

Soap (Vitra C.) 2.0%

AE (Berol 160) 3.5%

STPP (Janssen) 26.0%

Sodium carbonate 5.0%

Sodium sulphate 21.0%

Sodium meta-silicate (BHD 26186) 8.0%

Sodium perborate (Fluka 71480) 14.0%

TAED 1.5%

EDTA 0.2%

Water to 100%

The lipase efficacy was checked in a 4-cycle-soil-wash procedure. After the wash the swatches were dried at room temperature for 16 hours and then re-soiled and stored 1–3 days before the next wash. The detergent dosage was 5 g/l and the following conditions were used:

Machine: Tergotometer Temperature: 30° C.

Water: 18° dH Swatch/wash liquid: 1 swatch/l pH: 10.0 Textile: cotton

Time: 30 minutes Swatch size: 7×50 cm

Soiling: The swatches were soiled with a combination of a lipid/protein/clay emulsion of following composition:

Olive oil (Sigma 01500) 14.4%

Stearic acid (Sigman S 4876) 1.8%

Monoglyceride (Grindtek MSP 90) 1.8%

Gelatine (Oxoid) 0.9%

Kaolin (Sigma K 7375) 1.4%

Carbon black (Degussa, Spezial schwarz 4) 0.2%

Indian ink (Rotring) 0.2%

Water 79.4%

Evaluation

Remission of the swatches was measured at 460 nm after each wash. The residual fatty matter content was determined gravimetrically after a Soxhlet extraction (5 hours, hexane). Dosage The enzymatic activities were dosed at a level equivalent to the reference examples.

Figure 1:
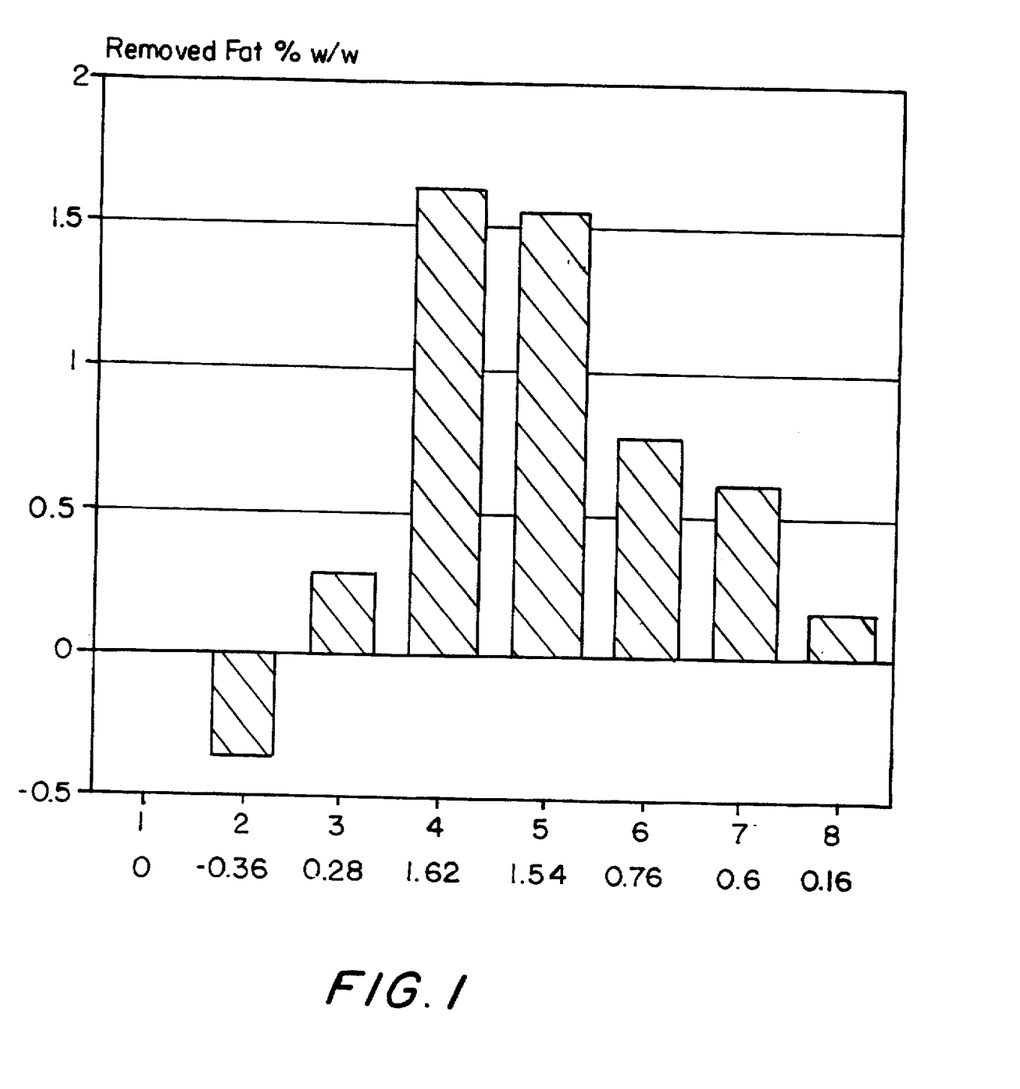
FIG. 1 shows lipase efficacy in washing performance tests using SP 341 lipase and proteases.
Figure 2:
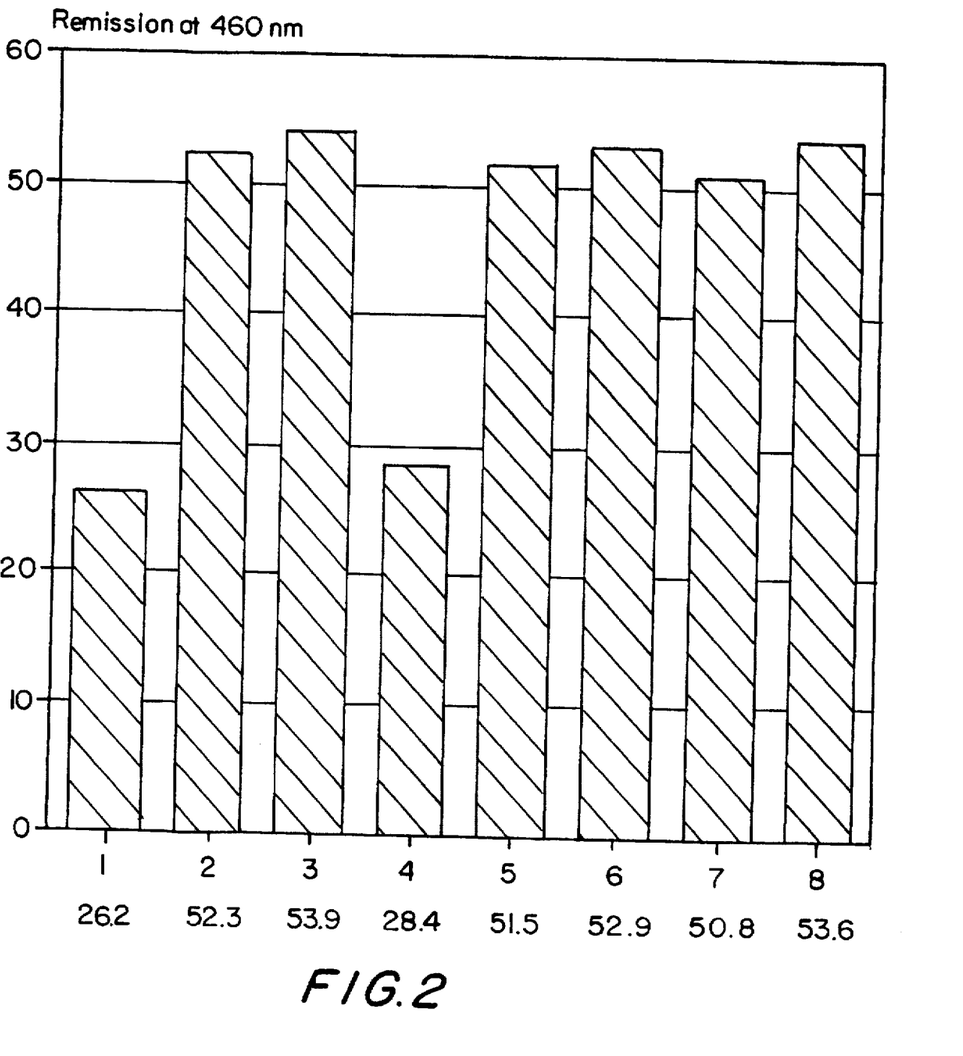
FIG. 2 shows overall performance in washing performance tests using SP 341 lipase and proteases.

The results from the performance test were listed in FIGS. 1 and 2. FIG. 1 shows the lipase efficacy whereas FIG. 2 shows the overall performance measured as remission of the swatches. The significance of the upper numerals along the abscissa on FIG. 1 is as follows:

1. Detergent
2. Detergent+Alcalase® 2.0 T (0.05 AU/l)
3. Detergent+Savinase® 4.0 T (0.15 KNPU/l)
4. Detergent+SP 341 (3000 LU/l)

20

5. Detergent+Alcalase®/SP 341 (Granulate of Example 9)
6. Detergent+SP 341+Alcalase® 2.0 T
7. Detergent+Savinase®/SP 341 (Granulate of Example 10)
8. Detergent+SP 341+Savinase® 4.0 T The significance of the upper numerals along the abscissa on FIG. 2 is as follows:

1. Detergent
2. Detergent+Alcalase® 2.0 T (0.05 AU/l)
3. Detergent+Savinase® 4.0 T (0.15 KNPU/l)
4. Detergent+SP 341 (3000 LU/l)
5. Detergent+Alcalase®/SP 341 (Granulate of Example 9)
6. Detergent+SP 341+Alcalase® 2.0 T
7. Detergent+Savinase®/SP 341 (Granulate of Example 10)
8. Detergent+SP 341+Savinase® 4.0 T The following Table shows the total amount of fatty matter left on the swatches after 4 washes:

| Trial | Residual fat |
| --- | --- |
| 1. | 5.31% |
| 2. | 5.67% |
| 3. | 5.03% |
| 4. | 3.69% |
| 5. | 3.77% |
| 6. | 4.55% |
| 7. | 4.71% |
| 8. | 5.15% |

Comments

FIG. 1

The SP 341 lipase (4) exhibits the major efficacy to remove fats. The combination of Alcalase® encapsulated with a hydrophobic agent and SP 341 (5) generates nearly the same effect. The combination of conventional Alcalase® and SP 341 (6) only exhibits half of this efficacy. The same trend is seen for the Savinase® case (7–8), but the SP 341 seems to be more sensitive to Savinase® than to Alcalase®.

FIG. 2

The remission measurements show that the protease performance dominates. In all cases where protease was present the overall performance was close to a remission around 50 units. The SP 341 only shows a marginal effect compared to the detergent alone.

Example 18

Figure 3:
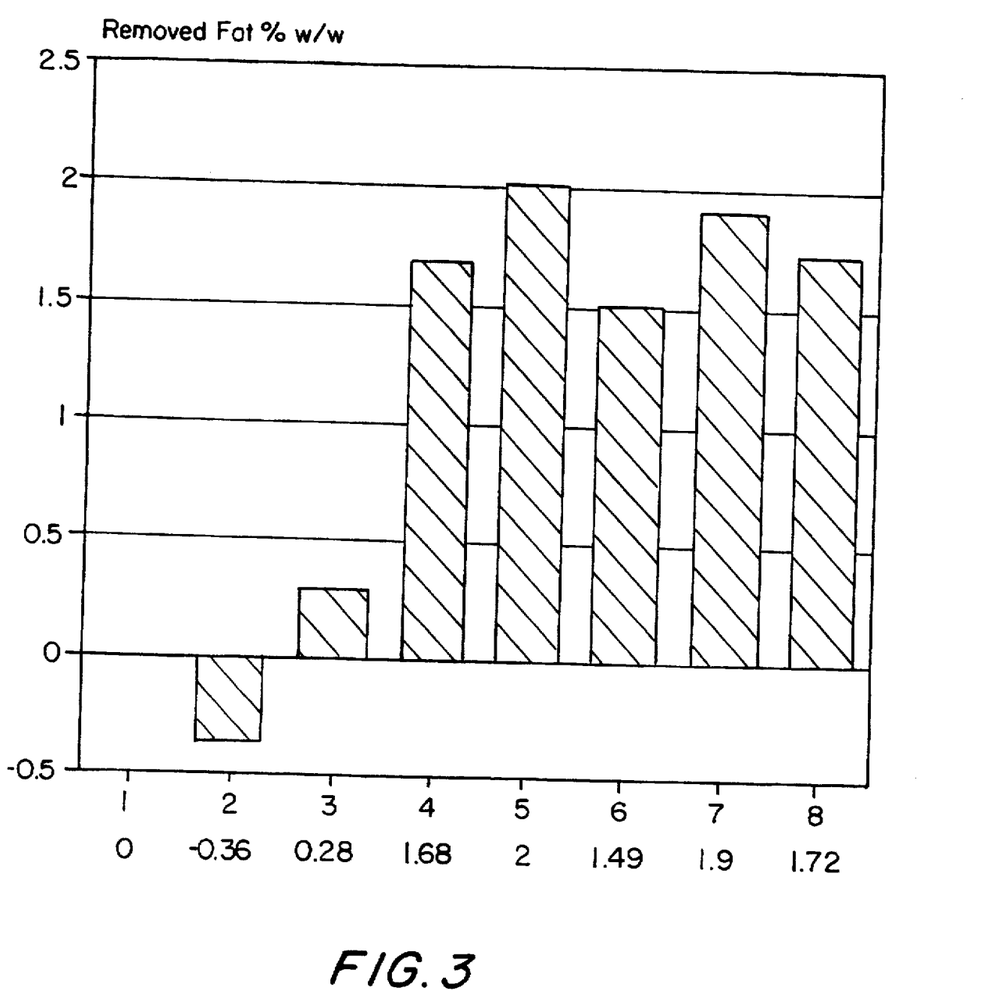
FIG. 3 shows lipase efficacy in washing performance tests using Lipolase and proteases.
Figure 4:
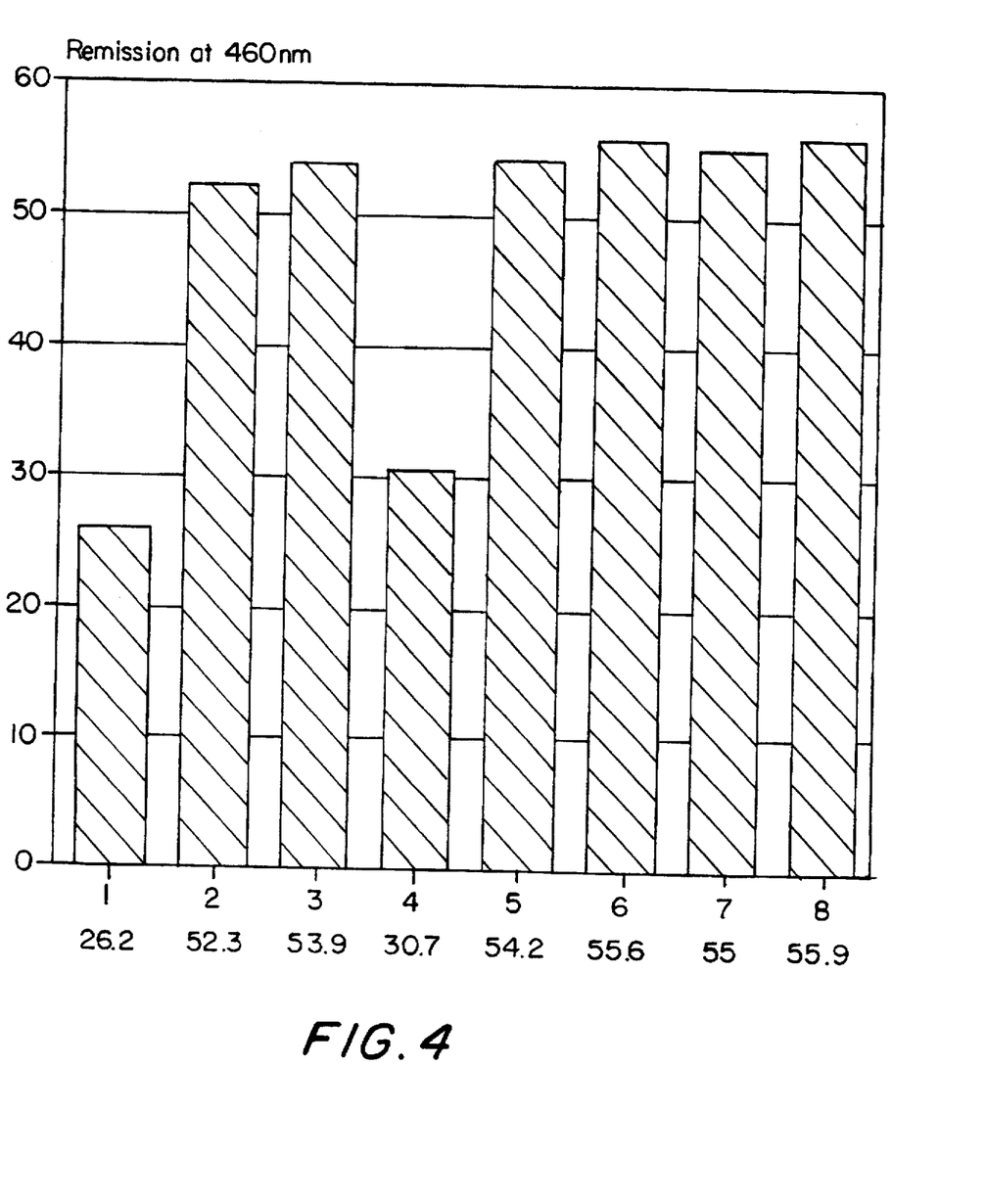
FIG. 4 shows overall performance in washing performance tests using Lipolase and proteases.

The results from the performance test are listed in FIGS. 3 and 4. The efficacy of the lipase is listed in FIG. 3 whereas FIG. 4 shows the overall performance measured as remission of the swatches.

The significance of the upper numerals along the abscissa on FIG. 3 is as follows:

1. Detergent
2. Detergent+Alcalase® 2.0 T (0.05 AU/l)
3. Detergent+Savinase® 4.0 T (0.15 KNPU/l)
4. Detergent+Lipolase® 100 T (3000 LU/l)
5. Detergent+Alcalase®/Lipolase® (Granulate of Example 11)
6. Detergent+Lipolase® 100 T+Alcalase® 2.0 T
7. Detergent+Lipolase® 100 T+Savinase® 4.0 T (coated with MSP 90)
8. Detergent+Lipolase® 100 T+Savinase® 4.0 T The significance of the upper numerals along the abscissa on FIG. 4 is as follows.

1. Detergent
2. Detergent+Alcalase® 2.0 T (0.05 AU/l)
3. Detergent+Savinase® 4.0 T (0.15 KNPU/l)
4. Detergent+Lipolase® 100 T (3000 LU/l)
5. Detergent+Alcalase®/Lipolase® (Granulate of Example 11)
6. Detergent+Lipolase® 100 T+Alcalase® 2.0 T
7. Detergent+Lipolase® 100 T+Savinase® 4.0 T (coated with MSP 90)
8. Detergent+Lipolase® 100 T+Savinase® 4.0 T The following Table shows the total amount of fatty matter left on the swatches after 4 washes.

| Trial | Residual fat |
| --- | --- |
| 1. | 5.31% |
| 2. | 5.67% |
| 3. | 5.03% |
| 4. | 3.63% |
| 5. | 3.31% |
| 6. | 3.82% |
| 7. | 3.41% |
| 8. | 3.59% |

Comments
FIG.3

Lipolase® is not as sensitive to proteases as SP 341. Still there is observed a small decrease in performance in the trials 6 and 8 where the proteases were released immediately compared to the sustained release coated preparations 5 and 7.

FIG. 4

Again the overall performance is dominated by the proteases. Lipolase® alone gives a better result than SP 341 in Example 9 but still only marginal efficacy compared to the proteases.

Example 19

15 kg of a powder composition with the formulation:

15% fibrous cellulose, ARBOCEL BC 200

15% optical brightener, TINOPAL DMS-X conc. CIBA GEIGY

4% kaolin SPESWHITE ECC

12% carbohydrate binder

54% finely ground sodium sulphate was granulated in a Lödige mixer FM 50 with pure water as granulating agent as described in U.S. Pat. No. 4.106.991, Example 1.

The granulate is dried on a fluid bed to a water content below 1% and finally sifted to get a product with particle range 300 µm to 900 µm.

7 kg of a granulate produced as described above with particle size between 300–900 µm is coated with a layer of glyceryl stearate/palmitate Grindtek MSP 90 (melting point 68° C.) and bentonite ASB 350 ECC in the following manner.

The granulate was heated to 75°–80° C. in a 20 l heat jacketed Lödige mixer which temperature was kept during the whole coating process. The heated granulate was mixed and sprayed with 700 g melted MSP90 followed by a powdering with 1000 g bentonite followed by spraying with 210 g MSP90 followed by powdering with 1000 g MSP90 followed by spraying with 210 g MSP90.

The granulate was finally cooled to room temperature on a fluid bed and sifted between 300 and 1000 µm.

A granulate with an inner core containing an optical brightener and an outer shell containing a proteolytic enzyme with the core and the shell separated by a protective layer was produced in the following manner.

6 kg of a shell material with the composition:

2.5 kg SAVINASE® conc. with proteolytic activity 37 KNPU/g 0.5 kg fibrous cellulose ARBOCEL BC 200

0.6 kg carbohydrate binder 0.2 kg kaolin SPESWHITE ECC 1.2 kg finely ground sodium sulphate is mixed and layered on the surface of 8 kg of granulate produced as described above in a manner as described in Example 1, except that in the present example the core contains an optical brightener and that a 50 l Lödige mixer FM 50 was used.

The granulate was finally dried to a water content below 1% and sifted between 300 and 1000 µm.

The granulate had proteolytic activity of 6.0 KNPU/g.

Example 20

7 kg of granulate as produced as described in Example 19 was coated with a layer of sodium thiosulphate and kaolin by a conventional fluid bed coating process.

280 g sodium thiosulphate and 280 g kaolin SPESWHITE ECC were dissolved/dispersed in 1000 g of water and sprayed onto the 7 kg of granulate in a Glatt WSG 5 fluid bed with continuous layering and drying.

Air inlet temperature 50° C. Air outlet temperature 35° C.

The process was concluded with a 5 min. drying period with air inlet temperature 50° C.

The granulate had a proteolytic activity of 5.2 KNPU/g.

Example 21

7 kg of granulate produced as described in Example 20 was coated with a protective coating of 280 g Grindtek MSP90 followed by 875 g titanium dioxide: Kaolin (SPESWHITE) 1:1 followed by 140 g Grindtek MSP90 as described in example 19.

The granulate was cooled to room temperature on a fluid bed and sifted between 300 and 1000 µm.

The granulate had a proteolytic activity of 4.7 KNPU/g. Stability test of granulates in Examples 19, 20 and 21

The stability test was made at a temperature of 37° C. and a humidity of 70%.

| | | 7 days | | 17 days | |
| --- | --- | --- | --- | --- | --- |
| Sample | 0 day KNPU/g | KNPU/g | Residual act. | KNPU/g | Residual act. |
| Ex. 19 | 6.00 | 2.56 | 42.7% | 2.25 | 37.5% |
| Ex. 20 | 5.20 | 3.50 | 67.3% | 2.71 | 52.1% |
| Ex. 21 | 4.70 | 3.05 | 64.9% | 2.50 | 53.2% |

The above data indicates that the final dust suppressing and protective coating generates an increased stability.

Example 22

14,7 of a powder composition with the formulation 2.2 kg fibrous cellulose, ARBOCEL BC 200

1.2 kg bentonite, ASB 350, ECC 1.8 kg carbohydrate binder 9.5 kg TAED was granulated in a Lödige mixer FM 50 with 3.0 kg of a 2% aqueous solution of a carbohydrate binder in the manner described in U.S. Pat. No. 4,106,991, Example 1.

In a fluid bed the granulate was dried to a water content below 1% and finally sifted to obtain a product with particle range 300 μm to 900 μm.

10 kg of dry 300–900 μm product was subsequently coated with 8.0% of hydrogenated tallow (melting point 59° C.) and 28% kaolin, Speswhite ECC, in the manner described in Example 19 except that the tallow was applied in one single (first) step followed by powdering with kaolin.

A granulate with an inner core containing TAED and an outer shell containing a proteolytic enzyme with the core and the shell separated by a protective layer was produced in the following manner.

10 kg of the tallow coated TAED containing granulate was cooled to room temperature and then transferred to a Lödige mixer FM 50 and in a first step sprayed with 200 g PEG 300 followed by layering of 4.6 kg of shell material mixture with the composition:

0.6 kg SAVINASE® concentrate, 50 KNPU/g 0.5 kg fibrous cellulose, Arbocel BC200

0.2 kg titanium dioxide 0.3 kg kaolin, Speswhite ECC 0.2 kg carbohydrate binder 2.8 kg finely ground sodium sulphate The shell was supplied with 1.4 kg of a 28.5% aqueous solution of a carbohydrate binder in the manner described in Example 1, except that in the present example the core contains a perborate activator, TAED, and that a 50 l Lödige mixer was used.

The granulate was finally dried to a water content below 1% and sieved to between 300 μm and 1000 μm.

Example 23

A TAED containing granulate coated with hydrogenated tallow was produced as described in Example 22, except that 20% kaolin was used in the wax coating step.

A granulate with an inner core containing TAED and an outer shell containing an optical brightener and with the core and the shell separated by a protective layer was produced in the following manner.

10 kg of the tallow coated TAED containing granulate was cooled to room temperature and then transferred to a Lödige mixer FM 50 and in a first step sprayed with 200 g PEG 300 followed by layering of 4.6 kg of shell material mixture with the composition:

0.75 kg optical brightener, Tinopal DMS-X, Ciba-Geigy 0.75 kg fibrous cellulose, Arbocel BC200

0.20 kg titanium dioxide 0.30 kg bentonite ASB 350, ECC 0.20 kg carbohydrate binder 2.40 kg finely ground sodium sulphate The shell was supplied with a continuous self-regulating loss-in-weight powder dosing system with a powder dosing rate of 20 kg/h. As a total 1.4 kg of an 28.5% aqueous carbohydrate binder solution was sprayed to bind the powder to the surface of the core particles. Otherwise the layering was applied as described in PCT WO 89/08695, Example 1.

The granulate was finally dried to a water content below 1% and sieved to obtain a product with particle range 300–900 μm.

Example 24

10 kg of SAVINASE® granulate with particle sizes between 300 μm and 700 μm produced as described in U.S. Pat. No. 4,106,991, Example 1, except that it was based on sodium sulphate, was coated with 8% of hydrogenated tallow and 26% of kaolin, as described in Example 22.

A granulate with an inner core containing the proteolytic enzyme SAVINASE® and an outer shell containing an optical brightener with the core and the shell separated by a protective layer, was produced in the following manner.

10 kg of the tallow coated Savinase® containing granulate was cooled to room temperature and then transferred to a Lödige mixer FM 50 and in a first step sprayed with 200 g PEG 300 followed by layering of 9.2 kg of a shell material mixture with the composition:

1.5 kg optical brightener, Tinopal DMS-X, Ciba-Geigy 1.0 kg fibrous cellulose, Arbocel BC200

0.4 kg titanium dioxide 0.6 kg kaolin, Speswhite ECC 0.4 kg carbohydrate binder 5.3 kg finely ground sodium sulphate The shell was supplied with a continuous self-regulating loss-in-weight powder dosing system with a powder dosing rate of 20 kg/h and with a total of 2.6 kg of an 26.2% aqueous carbohydrate binder solution, and otherwise as described in PCT WO 89/08695, Example 1.

The granulate was finally dried to a water content below 1% and sieved to obtain a product with particle range 300–900 μm.

Example 25

10 kg of SAVINASE® granulate with particle range between 300 μm and 1000 μm produced as described in U.S. Pat. No. 4,106,991, Example 1, except that it was based on sodium sulphate, was coated with 10% of hydrogenated tallow and 30% of kaolin, as described in Example 22.

A granulate with an inner core containing the proteolytic enzyme SAVINASE® and an outer shell containing a chlorine scavenger, whereby the core and the shell was separated by a protective layer was produced in the following manner.

10 kg of the tallow coated SAVINASE® containing granulate was transferred to a Lödige mixer FM 50 at 60° C. and kept at this temperature during the layering process by use of 60° C. hot water in the mixer heating jacket.

9.2 of shell material with the composition:

6.8 kg ammonium sulphate 1.0 kg fibrous cellulose, Arbocel BC200

0.2 kg titanium dioxide 0.7 kg kaolin, Speswhite ECC 0.5 kg carbohydrate binder was supplied with a continuous self-regulating loss-in-weight powder dosing system with a powder dosing rate of 50 kg/h and with a total of 2.1 kg of a 34.7% aqueous carbohydrate binder solution (the binder solution had been slightly acidified with 0.7% citric acid to suppress ammonia evaporation/smell during the granulation). Otherwise the layering was applied as described in PCT WO 89/08695, Example 1.

The granulate was finally dried to a water content below 1% and sieved to obtain a product with particle range 300–1000 μm.

Example 26

10 kg of SAVINASE® granulate with particle range between 300 μm and 1000 μm produced as described in U.S.

Pat. No. 4,106,991, Example 1, except that it was based on sodium sulphate, was coated with 5% of hydrogenated tallow and 15% of kaolin, as described in Example 22.

A granulate with an inner core containing the proteolytic enzyme SAVINASE® and an outer shell containing a chlorine scavenger, whereby the core and the shell was separated by a protective layer, was produced in the manner described in Example 25.

Example 27

10 kg of SAVINASE® granulate with particle range between 300 μm and 1000 μm produced as described in U.S. Pat. No. 4,106,991, Example 1, except that it was based on sodium sulphate, was coated with 3% of hydrogenated tallow and 10% of kaolin, as described in Example 22.

A granulate with an inner core containing the proteolytic enzyme SAVINASE® and an outer shell containing a chlorine scavenger, whereby the core and the shell was separated by a protective layer, was produced in the manner described in Example 25.

Example 28

10 kg of ALCALASE® granulate with particle range between 300 μm and 1000 μm, produced as described in U.S. Pat. No. 4,106,991, Example 1, except that it was based on sodium sulphate, was coated with 5% of hydrogenated fatty acid (melting point 58° C.) and 16% of kaolin as described in Example 22.

A granulate with an inner core containing the proteolytic enzyme ALCALASE® and an outer shell containing a chlorine scavenger, whereby the core and the shell was separated by a protective layer, was produced in the following manner.

10 kg of the tallow coated ALCALASE® containing granulate was transferred to a Lödige mixer FM 50 at 60° C. and kept at this temperature during the layering process by use of 60° C. hot water in the mixer heating jacket.

9.2 of shell material with the composition:

7.0 kg ammonium sulphate 1.0 kg fibrous cellulose, Arbocel BC200

0.7 kg kaolin, Speswhite ECC 0.5 kg carbohydrate binder was applied as described in Example 25. The granulate was finally dried to a water content below 1% and sieved to obtain a product with particle range 300–1000 μm.

Washing experiments with granulates from Examples 25, 26 and 27

Test: Wash test with granulates containing chlorine scavengers.

Principle: Terg-o-tometer, 100 rpm.

Water: 6° dH (33% tap water, 67% deionized water)

Temperature: 40°C.

Time: 15 min.

After 15 min. wash, $Na_2S_2O_3$ was added to all the beakers (during a time period of 14 min). Then the swatches were rinsed.

Detergent: 1 g/l US base powder pH: measured to: 9.2

Textile/liquid ratio:

8 swatches/800 ml (the dimensions of each swatch was 7×7 cm)

Rinsing: 10+15 min. in running tap water

Test material: Pre-rinsed grass on cotton

Enzymes: Savinase® (Ref) 7.04 KNPU(S)/g

Savinase granulates, Ex. 9 3.84

Savinase granulates, Ex. 10 4.40

Savinase granulates, Ex. 11 4.61

Enzyme dosage: 0–0.09 KNPU/l

Hypochlorite dosage:

0–4.5–9.0 ppm NaOCl

Repetitions: 2 independent repeats

Analysis: % remission at 460 nm on Elrepho 2000 (+UV)

Comments: The detergent was dissolved and heated to 40° C. in the Terg-o-tometer.

NaOCl, enzyme and test swatches were added in the order indicated within 60 seconds.

Results

| Enzyme | dosage KNPU/l | NaOCl ppm | % R | Δ R |
|---|---|---|---|---|
| — | 0 | 0 | 83.4 | |
| Savinase | 0.09 | 0 | 101.4 | 18.0 |
| Ex. 25 | 0.09 | 0 | 101.6 | 18.2 |
| Ex. 26 | 0.09 | 0 | 101.4 | 18.0 |
| Ex. 27 | 0.09 | 0 | 101.4 | 18.0 |
| — | 0 | 4.5 | 85.9 | |
| Savinase | 0.09 | 4.5 | 93.4 | 7.5 |
| Ex. 25 | 0.09 | 4.5 | 102.5 | 16.6 |
| Ex. 26 | 0.09 | 4.5 | 102.4 | 16.5 |
| Ex. 27 | 0.09 | 4.5 | 102.0 | 16.1 |
| — | 0 | 9 | 87.3 | |
| Savinase | 0.09 | 9 | 87.6 | 0.3 |
| Ex. 25 | 0.09 | 9 | 94.7 | 7.4 |
| Ex. 26 | 0.09 | 9 | 89.9 | 2.6 |
| Ex. 27 | 0.09 | 9 | 88.9 | 1.6 |

Comments

With no hypochlorite dosage practically exactly the same enzyme performance from the 4 granulates is observed, measured by ΔR. At a dosage of 4.5 ppm hypochlorite the performance of the Savinase® reference is reduced to approximately half the performance, measured by ΔR, while the three granulates from the examples still exhibit maximal performance. At the high dosage of hypochlorite no significant enzyme performance is observed in relation to the reference. The granulate from Example 25 still exhibits approx. 50% performance due to the high dosage of tallow which delays the release rate, combined with the chlorine scavenging agent.

We claim:

1. A granulate, comprising:
   (a) a core, wherein said core comprises:
      (i) a first enzyme;
      (ii) artificial or cellulose fibers;
      (iii) a binder;
      (iv) a filler; and
      (v) a granulating agent;
         wherein the enzyme is dispersed throughout the core, the core has a mean particle size between about 100 μm and 1000 μm, and wherein the core is in an amount between 10–50% by weight of the granulate; and
   (b) a shell surrounding said core, wherein the shell comprises
      (vi) artificial or cellulose fibers in an amount of 1.5–40 % by weight of the dry weight of the shell;
      (vii) a binder;
      (viii) a filler;
      (ix) a granulating agent; and
      (x) a second enzyme.

2. The granulate of claim 1, wherein the first and second enzymes are selected from the group consisting of proteases, amylases, lipases, cellulases and oxidases.

3. The granulate of claim 1, wherein the core is of a shape having a ratio between the largest and the smallest dimension which is below 3.

4. The granulate of claim 1, wherein the fibers have an average length of 50–2000 μm and an average width of 5–50 μm.

5. The granulate of claim 1, wherein the fibers are prepared from a polymer selected from the group consisting of polyethylene, polypropylene, polyester, polyvinylformal and poly(meth)acrylic polymers.

6. The granulate of claim 1, wherein the binder is selected from the group consisting of polyvinyl pyrrolidone, dextrins, polyvinyl alcohols, hydroxypropyl cellulose, methyl cellulose and carboxymethyl cellulose.

7. The granulate of claim 1, wherein the filler is selected from the group consisting of organic and inorganic salts.

8. The granulate of claim 1, wherein the core is surrounded by a coating of a sustained release agent which is surrounded by the shell.

9. The granulate of claim 8, wherein the first enzyme is a protease.

10. The granulate of claim 8, wherein the second enzyme is a lipase.

11. The granulate of claim 8, wherein the core comprises between 1.5 and 40% by weight of the artificial or cellulose fibers.

12. The granulate of claim 8, wherein the sustained release agent is a mixture of a mono- and diglyceride of a fatty acid.

13. The granulate of claim 1, wherein the core is surrounded by a coating of a protective agent which is surrounded by the shell.

14. The granulate of claim 13, wherein the core comprises the artificial or cellulose fibers in an amount of between 1.5 and 40% by weight of the core.

15. The granulate of claim 13, wherein the protective agent is selected from the group consisting of fatty acid esters, alkoxylated alcohols, polyvinyl alcohols, ethoxylated alkylphenols, polyethylene glycols, linear alcohol alkoxylates, polyvinyl pyrrolidones, polymeric nonylphenyl ethoxylates, dinonylphenyl ethoxylate, fatty acids, paraffins, waxes, mono-, di- or triglycerides of single fatty acids or mixed fatty acids, methyl cellulose, ethyl cellulose, hydroxypropyl cellulose and coconut monoethanol amide.

16. The granulate according to claim 15, wherein the protective agent is a mixture of a mono- and diglyceride.

17. The granulate of claim 13, wherein the protective agent comprises an antioxidant.

18. A method for producing the granulate of claim 1, comprising sequentially introducing into a granulating device (a) the core and (b) the fibers, the binder, the filler, the granulating agent and the second enzyme that form the shell.

19. The method according to claim 18, wherein the granulating device is a drum granulator.

20. The method according to claim 18, wherein the granulating agent comprises water and the method further comprises drying the resultant granulate.

21. The method according to claim 18, wherein the granulating agent comprises a waxy substance selected from the group consisting of polyglycols, fatty alcohols, ethoxylated fatty alcohols, higher fatty acids, mono-, di- and triglycerides of higher fatty acids, alkylaryl ethoxylates and coconut monoethanolamide.

22. A method for producing the granulate of claim 8, comprising sequentially introducing into a granulating device (a) the core, (b) the sustained release coating agent, and (c) the fibers, the binder, the filler, the granulating agent and the second enzyme that form the shell.

23. A method for producing the granulate of claim 13, comprising sequentially introducing into a granulating device (a) the core, (b) the protective agent, and (c) the fibers, the binder, the filler, the granulating agent and the second enzyme that form the shell.

* * * * *